US008865438B2

(12) United States Patent
Van Krieken et al.

(10) Patent No.: US 8,865,438 B2
(45) Date of Patent: Oct. 21, 2014

(54) PROCESS FOR THE PREPARATION OF A MONOVALENT SUCCINATE SALT

(75) Inventors: Jan Van Krieken, Gorinchem (NL); Jan Van Breugel, Woudrichem (NL)

(73) Assignee: Purac Biochem B.V., Gorinchem (NL)

( * ) Notice: Subject to any disclaimer, the term of this patent is extended or adjusted under 35 U.S.C. 154(b) by 333 days.

(21) Appl. No.: 13/132,277

(22) PCT Filed: Dec. 2, 2009

(86) PCT No.: PCT/EP2009/066238
§ 371 (c)(1),
(2), (4) Date: Jun. 1, 2011

(87) PCT Pub. No.: WO2010/063762
PCT Pub. Date: Jun. 10, 2010

(65) Prior Publication Data
US 2011/0244534 A1    Oct. 6, 2011

Related U.S. Application Data

(60) Provisional application No. 61/193,471, filed on Dec. 2, 2008.

(30) Foreign Application Priority Data

Dec. 2, 2008    (EP) .................................... 08170490

(51) Int. Cl.
| C12P 7/46 | (2006.01) |
|---|---|
| C12N 1/00 | (2006.01) |
| C07C 51/41 | (2006.01) |
| C12N 1/26 | (2006.01) |

(52) U.S. Cl.
CPC ... *C12P 7/46* (2013.01); *C12N 1/26* (2013.01); *C07C 51/412* (2013.01)
USPC .......................................... 435/145; 435/243

(58) Field of Classification Search
CPC ........................................................ C12P 7/46
USPC ........................................................ 435/145
See application file for complete search history.

(56) References Cited

U.S. PATENT DOCUMENTS

| 5,168,055 A | 12/1992 | Datta |
|---|---|---|
| 5,958,744 A | 9/1999 | Berglund |
| 7,217,837 B2 * | 5/2007 | Isotani .......................... 562/593 |
| 7,563,606 B2 * | 7/2009 | Aoyama et al. ............... 435/145 |
| 2006/0276674 A1 | 12/2006 | Kushiku |
| 2006/0281156 A1 * | 12/2006 | Aoyama et al. ............... 435/145 |
| 2007/0015264 A1 | 1/2007 | Isotani |
| 2010/0094051 A1 | 4/2010 | Nishi |

FOREIGN PATENT DOCUMENTS

| CN | 101348429 | 1/2009 |
|---|---|---|
| EP | 1669459 A1 | 6/2006 |
| EP | 1672067 A1 | 6/2006 |
| EP | 1686183 A1 | 8/2006 |
| FR | 2925068 A1 | 6/2009 |
| GB | 1011506 | 12/1965 |
| WO | WO2008143015 | 5/2008 |

OTHER PUBLICATIONS

European Search Report of the European Patent Office Patent Office in counterpart foreign application No. PCT/EP2009/066238 filed Dec. 2, 2009.
Written Opinion of the European Patent Office Patent Office in counterpart foreign application No. PCT/EP2009/066238 filed Dec. 2, 2009.

* cited by examiner

*Primary Examiner* — Yong Pak
(74) *Attorney, Agent, or Firm* — Peter J. Ims; Westman, Champlin & Koehler, P.A.

(57) ABSTRACT

A process for the preparation of a monovalent succinate salt includes:

a) fermenting a carbohydrate source to succinic acid by means of a micro-organism, b) adding a alkaline earth metal hydroxide, carbonate and/or hydrogencarbonate, the alkaline earth metal being calcium or magnesium, as neutralising agent during the fermentation in an aqueous medium and causing the formation of calcium succinate or magnesium succinate, c) reacting the alkaline earth metal succinate salt in an aqueous medium with a monovalent hydroxide, carbonate and/or hydrogencarbonate base to form an alkaline earth metal hydroxide, carbonate and/or hydrogencarbonate and a monovalent succinate salt, d) separating the monovalent succinate salt from the alkaline earth metal hydroxide, carbonate and/or hydrogencarbonate, and e) recycling the alkaline earth metal hydroxide, carbonate and/or hydrogencarbonate to step b.

5 Claims, No Drawings

PROCESS FOR THE PREPARATION OF A MONOVALENT SUCCINATE SALT

CROSS-REFERENCE TO RELATED APPLICATION

This Application is a Section 371 National Stage Application of International Application No. PCT/EP2009/066238, filed Dec. 2, 2009 and published as WO 2010/063762A2 on Jun. 10, 2010, in English, which in turn is based on and claims benefit of US Provisional Application No. 61/193,471, filed Dec. 2, 2008.

BACKGROUND

The discussion below is merely provided for general background information and is not intended to be used as an aid in determining the scope of the claimed subject matter.

Aspects of the present invention relate to a process for the preparation of monovalent succinate salts. Aspects of the present invention also pertain to an integrated fermentation and salt exchange process for the manufacture of monovalent succinate salts.

Succinic acid, also known as butanedioic acid and ethanedicarboxylic acid, is a compound which is suitable for a variety of uses. It finds application in food, pharmaceuticals, cosmetics, and as a starting material for chemical applications. For example, it may be used as a starting material for the production of 1,4-butanediol, tetrahydrofuran, and gamma-butyrolactone.

Succinic acid may be prepared via fermentation of carbohydrates by micro-organisms. A common feature to all fermentation processes wherein acid is manufactured is the need to neutralize the acids excreted by the micro-organisms in the process. If the acids are not neutralized, the pH of the fermentation process will decrease. When the pH drops below a critical value, depending on the micro-organism used in the process, the micro-organism's metabolic process may be damaged, and the fermentation process brought to a halt. It is therefore common practice to add a base during the fermentation process to keep the pH of the fermentation mixture at a specified value.

There are a number of compounds suitable as neutralizing agent, and a number of manners in which the resulting materials can be processed further, there is still need for a process for manufacturing succinic acid compounds by fermentation which allows working with highly concentrated solutions, which gives a high yield of the desired compound without producing substantial amounts of non-reusable components, and which provides the succinic acid in a form which enables easy and efficient further processing.

SUMMARY

This Summary and the Abstract herein are provided to introduce a selection of concepts in a simplified form that are further described below in the Detailed Description. This Summary and the Abstract are not intended to identify key features or essential features of the claimed subject matter, nor are they intended to be used as an aid in determining the scope of the claimed subject matter. The claimed subject matter is not limited to implementations that solve any or all disadvantages noted in the Background.

An aspect of the present invention pertains to a process for the preparation of a monovalent succinate salt comprising the steps of:

a) fermenting a carbohydrate source to succinic acid by means of a micro-organism, b) adding a alkaline earth metal hydroxide, carbonate and/or hydrogencarbonate, the alkaline earth metal being calcium or magnesium, as neutralising agent during the fermentation under formation of an aqueous medium comprising calcium succinate or magnesium succinate, c) reacting the alkaline earth metal succinate salt in an aqueous medium with a monovalent hydroxide, carbonate and/or hydrogencarbonate base to form an alkaline earth metal hydroxide, carbonate and/or hydrogencarbonate and a monovalent succinate salt, d) separating the monovalent succinate salt from the alkaline earth metal hydroxide, carbonate and/or hydrogen carbonate, e) recycling the alkaline earth metal hydroxide, carbonate and/or hydrogencarbonate to step b.

DETAILED DESCRIPTION OF THE ILLUSTRATIVE EMBODIMENTS

It has been found that there is a specific relationship between the nature of the alkaline earth metal in the succinate and the nature of the base. For both calcium as well as magnesium succinate, the base is selected from the group consisting of sodium hydroxide, sodium carbonate, sodium hydrogencarbonate, potassium hydroxide, potassium carbonate and potassium hydrogencarbonate. More specifically, where the alkaline earth metal succinate salt is calcium succinate the base is selected from the group consisting of sodium hydroxide, sodium carbonate, sodium hydrogencarbonate, potassium hydroxide, potassium carbonate, potassium hydrogencarbonate, ammonium carbonate and ammonium hydrogencarbonate. It has been found that the use of these bases results in a very high yield being obtained, much higher than when, for example, ammonium hydroxide or triethyl amine is used. Where the alkaline earth metal succinate salt is magnesium succinate, the base is selected from the group consisting of sodium hydroxide, sodium carbonate, sodium hydrogencarbonate, potassium hydroxide, potassium carbonate and potassium hydrogencarbonate. Again, it has been found that the use of these specific compounds results in a very high yield being obtained, much higher than in the case of, for example, ammonium hydroxide, ammonium carbonate, or triethylamine. It is of particular interest to note that ammonium carbonate shows attractive results when used in combination with calcium succinate, but not when used in combination with magnesium succinate.

The high yields obtained in the salt exchange process according to the invention also result in the formation of high yields of magnesium or calcium carbonate, hydrogencarbonate and/or hydroxide, which can be recycled to the fermentation step. This makes for a low-waste, environmentally friendly process.

The succinate is finally obtained in the form of a monovalent salt. These monovalent salts are particularly suitable for further processing. Preferred monovalent salts are potassium and sodium succinate salts. Especially preferred is a sodium succinate salt.

The first step in the process is fermenting a carbohydrate source to succinic acid by means of a micro-organism. The nature of the carbohydrate source used for the process is not critical, even relatively raw carbohydrate sources can be used for the fermentation. Examples of suitable carbohydrate sources are sucrose, (liquefied) starch, and glucose syrup. Fermentation processes of this type are known in the art and require no further elucidation here.

During fermentation, an alkaline earth metal hydroxide, carbonate and/or hydrogencarbonate, the alkaline earth metal being calcium or magnesium, is added as neutralising agent. This results in the formation of an aqueous medium comprising the corresponding alkaline earth metal succinate salt of calcium or magnesium. The amount of base added is determined by the amount of succinate produced and may be determined via pH control of the fermentation medium.

An aspect of the present invention encompasses the use of calcium or the use of magnesium. Where calcium is used, calcium carbonate, calcium hydrogencarbonate and/or calcium hydroxide may be used. Calcium carbonate may be advantageous because it results in a product with a low solubility. Where magnesium is used, magnesium carbonate, magnesium hydrogencarbonate and/or magnesium hydroxide may be used. Magnesium hydroxide may be advantageous because it results in a product with a low solubility.

The next step is the salt exchange where the alkaline earth metal succinate salt is reacted with a monovalent base.

Optionally, the medium comprising the alkaline earth metal succinate is subjected to a step to remove the biomass from the medium before effecting the reaction with the monovalent hydroxide, carbonate and/or hydrogencarbonate base. Biomass removal may be effected, for example, by separation on size, e.g., through filtration, or by separation on density. Conventional methods include filtration, flotation, sedimentation, centrifugation, flocculation and combinations thereof. It is within the scope of the skilled person to determine an appropriate method. Other optional pre-treatment steps include washing, filtration, (re)crystallization and concentration, and combinations thereof.

The reaction of the alkaline earth metal succinate with the monovalent base takes place in an aqueous medium. The succinate is generally already present in an aqueous medium when it leaves the fermentation. Calcium succinate typically will be present in the fermentation medium in the solid state. Magnesium succinate typically will be present dissolved in the reaction medium.

Depending on the nature of the monovalent base, it may be added in solid form or dissolved or suspended in an aqueous medium. The amount of base is determined by stoichiometric and pH considerations. In general, the molar ratio between the base and the succinate is between 0.9:1 and 1.5:1, more in particular between 0.95:1 and 1.3:1. Under some conditions it may be advantageous to use a surplus of base to obtain a high conversion. In that case, it may be advantageous for the molar ratio between the base and the succinate to be between 5:1 and 3:1.

In an aspect of the invention, the reaction is carried out in two steps wherein in the first step the alkaline earth metal succinate is reacted with a monovalent base to form a monovalent succinate, and in a second step some further base is added to ensure the removal of virtually all alkaline earth metal ions from the succinate. This is relevant for preparing a product with a low alkaline earth metal ion content. This may be necessary because of product specifications or certain further processing steps such as membrane electrodialysis. Additional purification steps like ion exchange may be necessary to reach the desired alkaline earth metal content.

As indicated above, where the alkaline earth metal succinate is calcium succinate, the base may be selected from the group consisting of sodium hydroxide, sodium carbonate, sodium hydrogencarbonate, potassium hydroxide, potassium carbonate, potassium hydrogencarbonate, ammonium carbonate and ammonium hydrogencarbonate. Which compound is preferred will depend on whether it is desirable to manufacture sodium succinate, potassium succinate, or ammonium succinate. The manufacture of sodium or ammonium succinate may be desired, making the use of a sodium or ammonium compound advantageous. Within the group of sodium compounds, sodium carbonate may be preferred because it may give a higher conversion. The use of hydroxides may sometimes be of interest for economical reasons.

Where the alkaline earth metal succinate is magnesium succinate, the base may be selected from the group consisting of sodium hydroxide, sodium carbonate, sodium hydrogencarbonate, potassium hydroxide, potassium carbonate and potassium hydrogencarbonate. The use of a sodium compound, resulting in the manufacture of sodium succinate may be preferred. When a high conversion is aimed for, the use of a hydroxide, in particular sodium hydroxide is advantageous. On the other hand, for economical reasons the use of carbonate may sometimes be attractive.

An aspect of the present invention allows for the processing of concentrated solutions or suspensions of alkaline earth metal succinate. In particular, solutions or suspensions may be used with a concentration in the range of 4 to 40 wt. %, more in particular in the range of 10 to 25 wt. %. For magnesium succinate, a concentration in the range of 4 to 25 wt. % is typical, and more specifically the range of 10 to 25 wt. % may be utilized. For calcium succinate a concentration in the range of 4 to 40 wt. % is typical, more specifically the range of 10 to 25 wt. % may be utilized.

This results in monovalent succinate solutions of high concentration, for example in the range of 4 to 30 wt. % more in particular in the range of 8-30 wt. %.

The reaction between the alkaline earth metal succinate and the monovalent base can take place under intensive agitation. This can be done by means of conventional mixers and/or stirrers, for example in a stirred tank reactor.

The reaction between the alkaline earth metal succinate and the base can take place at a temperature between 20 and 100° C., more advantageously between 20 and 75° C.

In one embodiment, the process according to an aspect of the invention is carried out continuously. In other embodiments the process is carried out in batch or in fed batch.

The alkaline earth metal hydroxide, carbonate and/or hydrogencarbonate and the monovalent succinate salt formed in the process can be easily separated from each other. The alkaline earth metal hydroxide, carbonate and/or hydrogencarbonate is in solid, particulate, form while the monovalent succinate salt is dissolved in the aqueous medium. The two components can therefore easily be separated by conventional processes, for example filtration or sedimentation. Optionally, the alkaline earth metal hydroxide, carbonate and/or hydrogencarbonate particles are washed with water after separation. In the case of a continuous process the particles can be continuously removed from the reaction medium. In the case of a batch process it may be advantageous that the particles are removed from the reaction medium directly after formation or as soon as technically possible.

The alkaline earth metal hydroxide, carbonate and/or hydrogencarbonate is recycled to the fermentation step.

If so desired, the aqueous medium containing the monovalent succinate salt may be subjected to one or more further purification/modification steps, such as activated carbon treatment, extraction, electrodialysis, etcetera. These purification steps are known in the art and need no further elucidation here. The product of the process according to an aspect of the invention may very suitably be subjected to a modification step wherein, for instance, the succinate salt is converted into succinic acid. This results in a succinic acid of very high purity being formed. Said conversion may be conducted, for example, by means of bipolar electrodialysis or addition of a strong mineral acid. The monovalent succinate salt may also be converted into other succinate salts or into succinate esters like dimethyl or dibutyl succinate.

In the above, the integrated fermentation and salt exchange process according to the invention has been described. While the salt exchange process is of particular interest in the context of this integrated process, situations may be envisaged where the process is carried out in a different context. Therefore, an aspect of the present invention also pertains to a process for preparing a monovalent succinate salt from an alkaline earth metal succinate salt selected from calcium succinate and magnesium succinate, wherein the alkaline earth metal succinate salt is reacted in an aqueous medium with a monovalent hydroxide, carbonate and/or hydrogencarbonate base to form an alkaline earth metal hydroxide, carbonate and/or hydrogencarbonate and a monovalent succinate salt.

In one embodiment, where the alkaline earth metal succinate salt is calcium succinate the base is selected from the group consisting of sodium hydroxide, sodium carbonate, sodium hydrogencarbonate, potassium hydroxide, potassium carbonate, potassium hydrogencarbonate, ammonium carbonate and ammonium hydrogencarbonate. In another embodiment, where the alkaline earth metal succinate salt is magnesium succinate the base is selected from the group consisting of sodium hydroxide, sodium carbonate, sodium hydrogencarbonate, potassium hydroxide, potassium carbonate and potassium hydrogencarbonate.

Aspects of the present invention are further illustrated by the following Examples, without being limited thereto or thereby.

Example

Preparation of Starting Materials

For preparation of magnesium succinate in an aqueous medium (solution), 80.0 grams of succinic acid were dissolved in 1000.0 grams of water. After heating to 50° C., a stoichiometric amount of solid magnesium oxide (27.3 g) was added. To make sure all of the succinic acid would react, a small surplus (2.3 g) of MgO was added. Finally, the mixture was filtered over a Büchner funnel, equipped with a filter paper. The filtrate, being a 9.4% (w/w) solution of magnesium succinate, was collected.

Calcium succinate in an aqueous medium (suspension) was prepared in an analogous manner by letting succinic acid (80.0 g+4.2 g surplus in 1000.1 g water) react with solid calcium hydroxide (50.6 g). After filtration and washing with approx. 800 ml of demineralised water, the residue (calcium succinate) was collected and dried in a desiccation stove for 18 hours at 80° C. The calcium succinate was then suspended in water.

The slight surplus of reagents in both reactions was applied in order to obtain succinates with a minimal amount of impurities.

Experiments

Magnesium succinate and calcium succinate were reacted with various bases to investigate the effectivity of the process according to the invention.

The following bases were used:
sodium hydroxide [NaOH]
sodium carbonate [$Na_2CO_3$]
ammonium carbonate [$(NH_4)_2CO_3$] (for calcium succinate, comparative for magnesium succinate)
ammonium hydroxide [$NH_4OH$] (comparative)
trietylamine [$N(CH_2CH_3)_3$] (comparative)

The reactions were carried out in 500 ml beakers or Erlenmeyer flasks containing 100 ml of 10 wt % Mg-succinate or Ca-succinate in aqueous medium. Sodium carbonate and ammonium carbonate were added in solid form in stoichiometric amounts. Ammonia, NaOH and triethylamine were added in solute form, also in stoichiometric amounts. The reaction mixtures were stirred using a stirring bar and a magnetic stirrer.

TABLE 1

| Exp. | Reaction | m (Mg/Ca-Succ.) [g] | Base [g] |
|---|---|---|---|
| 1 | MgSucc + $NH_4OH$ | 99.7 | 9.2 |
| 2 | MgSucc + NaOH | 100.0 | 10.8 (+89.4 $H_2O$) |
| 3 | MgSucc + $Et_3N$ | 100.0 | 13.5 (+86.7 $H_2O$) |
| 4 | MgSucc + $Na_2CO_3$ | 99.9 | 7.2 |
| 5 | MgSucc + $(NH_4)_2CO_3$ | 99.6 | 6.5 |
| 6 | CaSucc + $NH_4OH$ | 10.0 + 89.8 $H_2O$ | 8.8 |
| 7 | CaSucc + NaOH | 10.0 + 90.1 $H_2O$ | 10.5 |
| 8 | CaSucc + $Et_3N$ | 9.9 + 90.3 $H_2O$ | 12.9 |
| 9 | CaSucc + $Na_2CO_3$ | 10.0 + 90.1 $H_2O$ | 6.8 |
| 10 | CaSucc + $(NH_4)_2CO_3$ | 10.0 + 90.1 $H_2O$ | 6.1 |

The mixtures were allowed to react for 1 hour.

From each reaction mixture, samples of 25 ml were taken. These were centrifuged, after which Mg (or Ca) and succinate were determined analytically. The analytical data and the initial concentration of Mg2+ or succinate were used for calculation of the conversion of Mg-succinate or Ca-succinate to Na—, $NH_4$— or triethyl-amine-succinate. The results are given in Table 2.

TABLE 2

| Experiment | pH | Mg/Ca [ppm] | Succinate [wt %] | Conversion [%] |
|---|---|---|---|---|
| 1: MgSucc + $NH_4OH$ (comparative) | 9.6 | 8415 | 6.9 | 43.0 |
| 2: MgSucc + NaOH (herein described) | 12.4 | 12 | 4.0 | 99.8 |
| 3: MgSucc + $Et_3N$ (comparative) | 9.6 | 3480 | 3.9 | 56.6 |
| 4: MgSucc + $Na_2CO_3$ (herein described) | 10.5 | 880 | 7.7 | 94.1 |
| 5: MgSucc + $(NH_4)_2CO_3$ (comparative) | 7.8 | 9487 | 7.5 | 37.4 |
| 6: CaSucc + $NH_4OH$ (comparative) | 11.1 | 3489 | 1.0 | 12.7 |
| 7: CaSucc + NaOH (herein described) | 13.0 | 281 | 6.5 | 95.4 |
| 8: CaSucc + $Et_3N$ (comparative) | 10.9 | 3297 | 1.0 | 13.3 |
| 9: CaSucc + $Na_2CO_3$ (herein described) | 10.5 | 19 | 7.0 | 99.3 |
| 10: CaSucc + $(NH_4)_2CO_3$ (herein described) | 8.0 | 829 | 7.0 | 98.7 |

As can be seen from Table 2, when sodium hydroxide is used, a conversion of well above 90% is obtained both for magnesium succinate and for calcium succinate. The same applies when sodium carbonate is used. For ammonium carbonate it should be noted that while for calcium succinate a conversion of 98.7% is obtained, the conversion for magnesium succinate is only 37.4%.

The invention claimed is:
1. A process for the preparation of a sodium and/or potassium succinate salt comprising the steps of:

a) fermenting a carbohydrate source to succinic acid with a micro-organism,
b) adding a alkaline earth metal hydroxide, carbonate and/or hydrogencarbonate, the alkaline earth metal being calcium or magnesium, as a neutralising agent during the fermentation in an aqueous medium and causing the formation of an alkaline earth metal succinate salt comprising calcium succinate or magnesium succinate,
c) reacting the alkaline earth metal succinate salt in the aqueous medium with a sodium and/or potassium hydroxide, carbonate and/or hydrogencarbonate base to form an alkaline earth metal hydroxide, carbonate and/or hydrogencarbonate and a sodium and/or potassium succinate salt,
d) separating the sodium and/or potassium succinate salt from the alkaline earth metal hydroxide, carbonate and/or hydrogencarbonate,
e) recycling the alkaline earth metal hydroxide, carbonate and/or hydrogencarbonate to step b, wherein the medium comprising the alkaline earth metal succinate is subjected to a step to remove the biomass from the medium before effecting the reaction with the hydroxide, carbonate or hydrogencarbonate base.

2. The process according to claim 1, wherein the alkaline earth metal succinate salt is reacted with a sodium hydroxide carbonate and/or hydrogencarbonate base.

3. The process according to claim 1, wherein the monovalent base is sodium hydroxide or sodium carbonate.

4. The process according to claim 1, wherein the concentration of the alkaline earth metal succinate in the aqueous medium is between 4 and 40 wt %.

5. The process according to claim 1 wherein the alkaline earth metal carbonate, hydroxide and/or hydrogencarbonate is separated from the sodium and/or potassium succinate salt by filtration.

* * * * *